United States Patent
Shiohama

(10) Patent No.: US 9,759,734 B2
(45) Date of Patent: Sep. 12, 2017

(54) ANALYZING APPARATUS CONTROL SYSTEM AND PROGRAM FOR THE SAME

(75) Inventor: Tohru Shiohama, Osaka (JP)

(73) Assignee: Shimadzu Corporation, Kyoto (JP)

( * ) Notice: Subject to any disclaimer, the term of this patent is extended or adjusted under 35 U.S.C. 154(b) by 976 days.

(21) Appl. No.: 13/552,457

(22) Filed: Jul. 18, 2012

(65) Prior Publication Data

US 2014/0020455 A1 Jan. 23, 2014

(51) Int. Cl.
*G01N 30/02* (2006.01)
*G01N 35/00* (2006.01)
*G01N 30/86* (2006.01)
*G01N 30/72* (2006.01)

(52) U.S. Cl.
CPC ..... *G01N 35/0092* (2013.01); *G01N 30/8644* (2013.01); *G01N 30/72* (2013.01); *G01N 2035/0094* (2013.01)

(58) Field of Classification Search
CPC ....... G01N 30/8644; G01N 2035/0094; G01N 30/72; G01N 35/0092; G01N 30/8624; G01N 30/8631
USPC ....................................... 73/61.55
See application file for complete search history.

(56) References Cited

U.S. PATENT DOCUMENTS 5,121,443 A * 6/1992 Tomlinson ......... G01N 30/8624
210/656

FOREIGN PATENT DOCUMENTS

| JP | 01-235849 | 9/1989 |
|---|---|---|
| JP | 04-138358 | 5/1992 |
| JP | 2005-083952 | 3/2005 |
| JP | 2009-008402 | 1/2009 |
| JP | 04-294271 | 7/2009 |
| JP | 2011-058982 | 3/2011 |

OTHER PUBLICATIONS

Machine translation of Shiohama [2011-058982] (abstract and original patent was provided by applicant), Mar. 24, 2011.*
Japanese Office Action mailed Jun. 4, 2013 for corresponding Japanese Patent App. No. 2010-002495.
English translation of "Reason for Rejection" for Japanese Office Action mailed on Jun. 4, 2013 for Japanese corresponding Patent App. No. 2010-002495.

* cited by examiner

*Primary Examiner* — Daniel S Larkin
(74) *Attorney, Agent, or Firm* — Morgan, Lewis & Bockius LLP

(57) ABSTRACT

The present invention aims at providing an analyzing apparatus control system which is capable of appropriately setting the conditions of measurement in an analyzing apparatus which is connected to a chromatograph, in which one more measurement events are performed based on a reference chromatogram. This system includes a measurement time range setting section for setting, for each of all peaks or previously selected peak or peaks included in a previously provided reference chromatogram which corresponds to the sample to be examined, the width of a peak as the measurement time range of the peak when the peak does not overlap another peak, or, when the peak overlaps another peak, the overall width of the peak and the overlapping peak as the measurement time range of the peak.

3 Claims, 5 Drawing Sheets

Fig. 8 Prior Art

ANALYZING APPARATUS CONTROL SYSTEM AND PROGRAM FOR THE SAME

TECHNICAL FIELD

The present invention relates to a system for controlling an analyzing apparatus and a program for this system. In particular, the present invention relates to a system and a program for setting conditions of an analysis in an analyzing apparatus which includes a chromatograph or is connected to a chromatograph.

BACKGROUND ART

In a chromatograph mass spectrometer, in which a chromatograph and a mass analyzer are combined, a sample is temporally separated by the chromatograph in the first stage, and then the separated sample is mass-analyzed in the mass analyzer in the subsequent stage (refer to Patent Document 1, for example).

In the mass analyzer of the subsequent stage, a measurement is usually not performed on the entire sample that has been temporally separated and introduced into the mass analyzer. Instead, a predetermined measurement is performed only on each area of fluctuation in the chromatogram, e.g. where a peak or peaks exist. That is, the measurement is performed only on one or more time ranges.

Therefore, a time range setting operation is required to perform an intended analysis. To do so, it is necessary to prepare a chromatograph of the same sample in advance for use as a reference by the user to set which measurement is performed at which point in time.

A control application for controlling an analyzing apparatus is used to set the time ranges. Conventionally, a user enters numbers to represent the time in predetermined entry fields while referring to a reference chromatograph. An example of the screen of such a conventional analyzing apparatus control application is shown in FIG. 7. In the left column of the example screen, the chromatograph measurement time ranges are divided into the following segments: "segment 1"=[0.000-10.000] (minutes) and "segment 2"=[10.000-20.000] (minutes). Measurements "event 1" and "event 2" in "segment 1", and measurement "event 1" in "segment 2" have been entered manually.

In a conventional chromatograph mass spectrometer, the time range for a measurement with certain conditions requires manual designation when setting the conditions of measurement for a mass analyzer, so the operation tends to be complicated, and it can cause input errors. Given this, the inventor of the present invention has already made an invention with the aim of providing an analyzing apparatus control system which allows users to set the conditions of analysis more understandably and simply than ever before. This invention has been filed prior to the present application and published as JP-A 2011-058982. This system provides a graphical user interface as shown in FIG. 9 and achieves such things as the effects below.

The time ranges of measurements are shown as range bars which are temporally superimposed on a reference chromatograph in a display unit (or monitor). This enables a user to immediately understand the relationship between the reference chromatogram and the measurements to be performed. Additionally, the relationships between multiple measurements that are performed on one sample are immediately visually recognized. Consequently, the burden of setting the conditions of measurements is alleviated and mistakes in the setting operation can be prevented.

The time range when the measurement will be performed can be altered by the user simply operating an input unit such as a mouse to adjust the length of a range bar or change its temporal position shown on the display unit. This enables a flexible setting of time ranges, facilitates operation, and also ensures a reduction of mistakes in the setting operation compared to the case where time ranges are set manually.

BACKGROUND ART DOCUMENT

Patent Document

[Patent Document 1] JP-A 2005-083952

DISCLOSURE OF THE INVENTION

Problems to be Solved by the Invention

Generally, time ranges for a measurement are manually set by the user based on his/her experience by utilizing conventional technologies as previously described. However, setting time ranges properly is not easy if the reference chromatogram has an issue such as a low resolution.

In some cases, if there are a large number of peaks for example, setting a time range properly for each peak requires a great amount of time and labor.

The problem to be solved by the present invention is to provide an analyzing apparatus control system capable of setting the conditions of measurements in an analyzing apparatus which is connected to a chromatograph and in which one or more measurements are performed in reference to a reference chromatogram. The present invention also aims at providing a program for the analyzing apparatus control system.

Means for Solving the Problem

To solve the aforementioned problem, the present invention provides an analyzing apparatus control system for controlling an analyzing apparatus so as to temporally separate a sample to be examined by a chromatograph, and perform a predetermined measurement in each of one or more measurement time ranges within a total measurement time, including:

a measurement time range setting section for setting, for each of all peaks or previously selected peak or peaks included in a previously provided reference chromatogram which corresponds to the sample to be examined, the width of a peak as the measurement time range of the peak when the peak does not overlap another peak, or, when the peak overlaps another peak, the overall width of the peak and the overlapping peak as the measurement time range of the peak.

To solve the aforementioned problem, the present invention also provides a program for an analyzing apparatus control system for controlling an analyzing apparatus so as to temporally separate a sample to be examined by a chromatograph, and perform a predetermined measurement in each of one or more measurement time ranges within a total measurement time, the program being for making a computer which executes the program functionate as a measurement time range setting section for setting, for each of all peaks or previously selected peak or peaks included in a previously provided reference chromatogram which corresponds to the sample to be examined, the width of a peak as the measurement time range of the peak when the peak does not overlap another peak, or, when the peak overlaps another peak, the overall width of the peak and the overlapping peak as the measurement time range of the peak.

The apparatus which is controlled by the analyzing apparatus control system according to the present invention can be any type of apparatus that analyzes and measures a sample that has been temporally separated by a chromatograph, such as a liquid chromatograph mass spectrometer.

Effects of the Invention

Appropriate measurement time ranges can always be set by means of the analyzing apparatus control system according to the present invention when measuring a sample to be measured which will be separated by the chromatograph. At the same time, it can reduce the workload because there will be no need for a user to set the details of the measurement time ranges.

Furthermore, the number of peaks to be measured can be increased, which can enhance the accuracy of the peak detection.

BRIEF DESCRIPTION OF THE DRAWINGS

Figure 8:
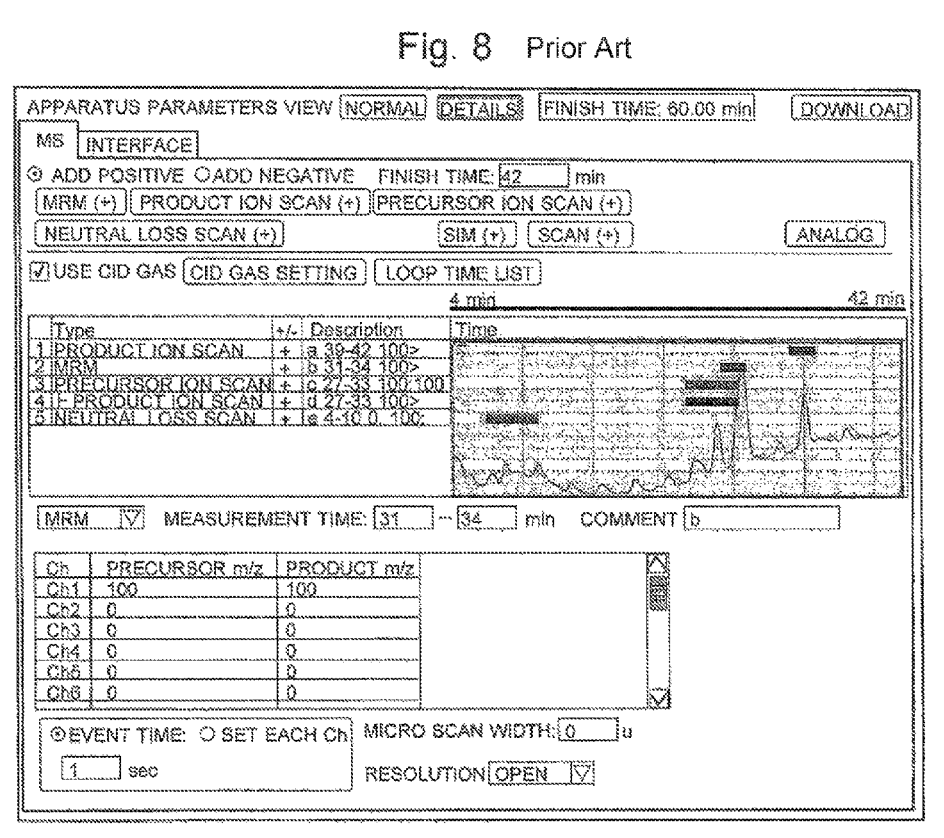

FIG. 8 shows an example of a screen of another conventional analyzing apparatus control application.

BEST MODE FOR CARRYING OUT THE INVENTION

Hereinafter, an example of the embodiment of the analyzing apparatus control system according to the present invention will be described in detail with reference to the figures.

Figure 1:
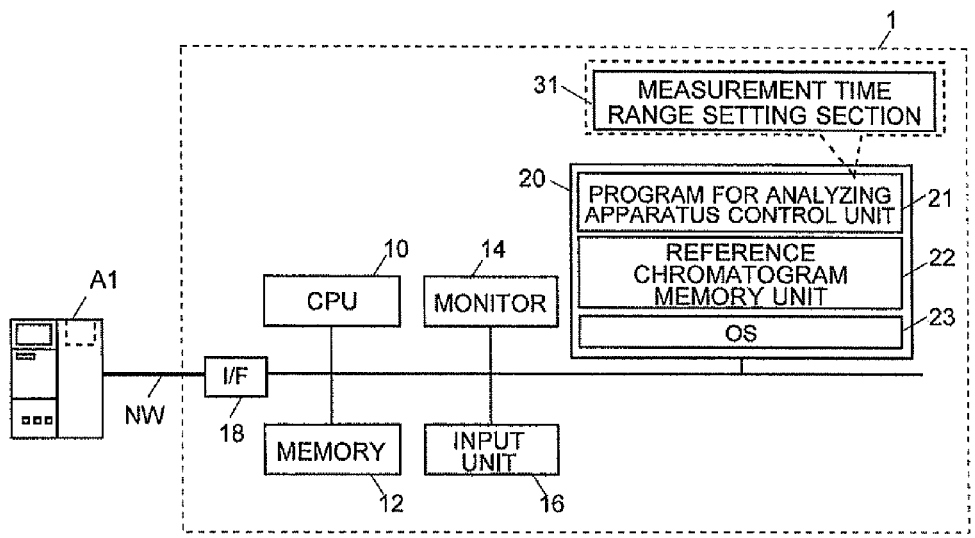
FIG. 1 is a schematic configuration of an embodiment of the analyzing apparatus control system according to the present invention.

FIG. 1 shows an embodiment of the analyzing apparatus control system 1 according to the present invention. The analyzing apparatus control system 1 is implemented by a computer, in which a memory 12, a monitor (display unit) 14 such as a liquid crystal display (LCD) 14, an input unit 16 such as a keyboard and a mouse, and a memory unit 20 such as a mass storage device, which is typically a hard disk drive or a solid state drive (SSD), are all connected to a central processing unit (CPU). A program 21 for an analyzing apparatus control system and a reference chromatogram memory unit 22 are stored in the memory unit 20. In the memory unit 20, an operating system (OS) 23 is also stored.

The analyzing apparatus control system 1 according to the present embodiment has an interface (I/F) 18 for controlling a direct connection with an external device or a connection through a network such as a Local Area Network (LAN). The analyzing apparatus control system 1 is connected with an analyzing apparatus A1, which is a chromatograph mass spectrometer. The analyzing apparatus control system according to the present invention does not necessarily have to be connected with an externally provided analyzing apparatus through the I/F 18, but may be integrated with an analyzing apparatus.

In the analyzing apparatus control system 1 according to the present embodiment, the OS 23 and the program 21 for an analyzing apparatus control system are provided separately. Of course, the program 21 for an analyzing apparatus control system may be integrated in a part of the OS 23.

FIG. 1 shows the analyzing apparatus control system 1 according to the present invention. In FIG. 1, a measurement time range setting section 31 is attached to the program 21 for an analyzing apparatus control system. The measurement time range setting section 31 is basically implemented as a software component when the CPU 10 executes the program 21 for an analyzing apparatus control system. Hereinafter, the program 21 for an analyzing apparatus control system may also be simply referred to as the "program 21."

Figure 2:
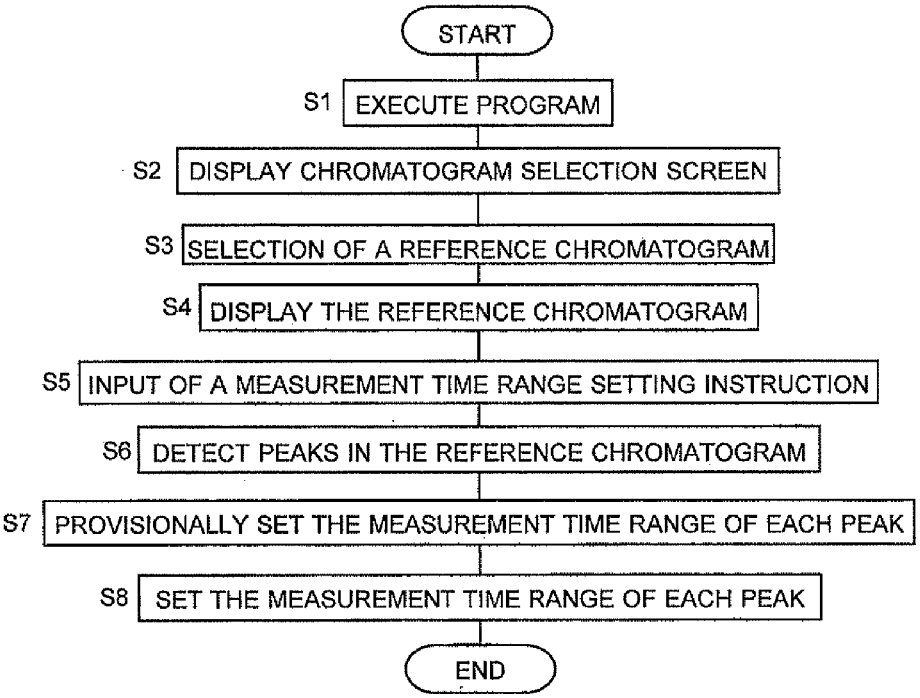
FIG. 2 is a flowchart showing an example of a process executed by the program for an analyzing apparatus control system according to the present embodiment.

Next, the operation of the analyzing apparatus control system 1 according to the present embodiment will be described with reference to FIG. 2, which is a flowchart showing an example of a process executed by the program for an analyzing apparatus control system according to the present embodiment.

First, a user instructs an execution of the program 21 for an analyzing apparatus control system by appropriate operation of the input unit 16 (e.g. double-clicks an icon displayed on the monitor 14) (Step S1). Based on the input of the instruction to execute the program 21 in Step S1, the CPU 10 executes the program 21 for an analyzing apparatus control system.

Then, when the user appropriately operates the input unit 16 (e.g. operates the mouse and presses a chromatogram selection button), the program 21 shows a chromatogram selection screen in which multiple chromatograms are listed which are stored in the reference chromatogram memory unit 22 so as to allow the user to select a chromatograph (Step S2).

The user appropriately operates the input unit 16 (e.g. operates the mouse and selects a compound from a compound list shown in the chromatogram selection screen) while looking at the chromatogram selection screen displayed in Step S2 in order to select a reference chromatogram corresponding to a sample to be measured (Step S3).

Figure 3:
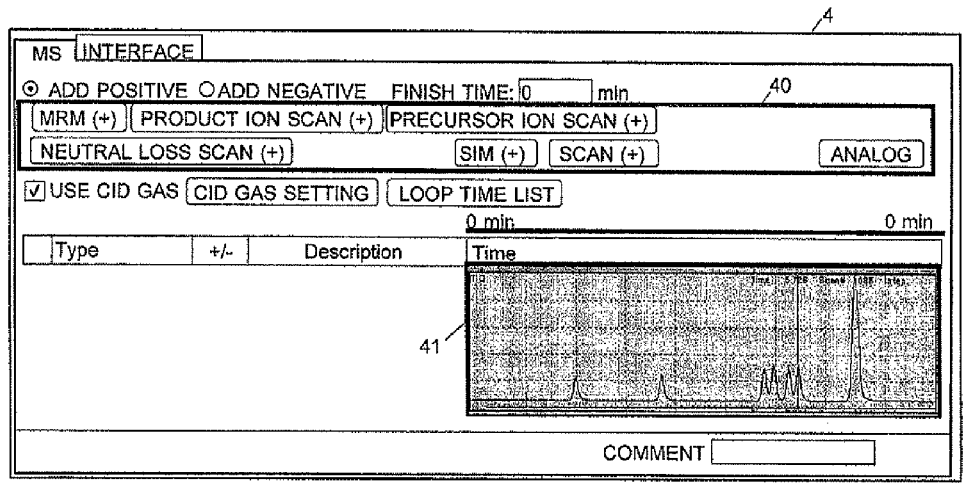
FIG. 3 shows an example of a chromatogram display screen.

When a reference chromatogram is selected in Step S3, the program 21 reads out the data of the specified reference chromatogram from among the multiple reference chromatograms which have been stored in advance in the reference chromatogram memory unit 22 and shows it in a chromatogram display area 41 of the chromatogram display screen 4, as shown in FIG. 3 (Step S4). The chromatogram display screen 4 includes a measurement addition button area 40 in addition to the chromatogram display area 41.

In the chromatogram display area 41, the entire reference chromatogram may be preferably displayed However, only a portion of the reference chromatogram may be displayed in the measurement time range display area 41 if the reference chromatogram is horizontally (i.e. in the time direction) long, or when a part of the reference chromatogram is enlarged. In this case, the program 21 responds to a user instruction to scroll (i.e. when a button for instructing a scroll to the right is pressed) by accordingly changing the display position of the reference chromatogram in the chromatogram display area 41.

Subsequently, when the user provides a measurement time range setting instruction (e.g. operates the mouse and presses a measurement time range setting button, which is not shown) in Step S5, the measurement time range setting section 31 of the program 21 performs a waveform separation of the reference chromatogram to detect peaks included in the reference chromatogram (Step S6). In the case where peak information of the reference chromatogram is available, the peak detection in S6 may be performed by reading out the available peak information, rather than performing a waveform separation.

Figure 4:
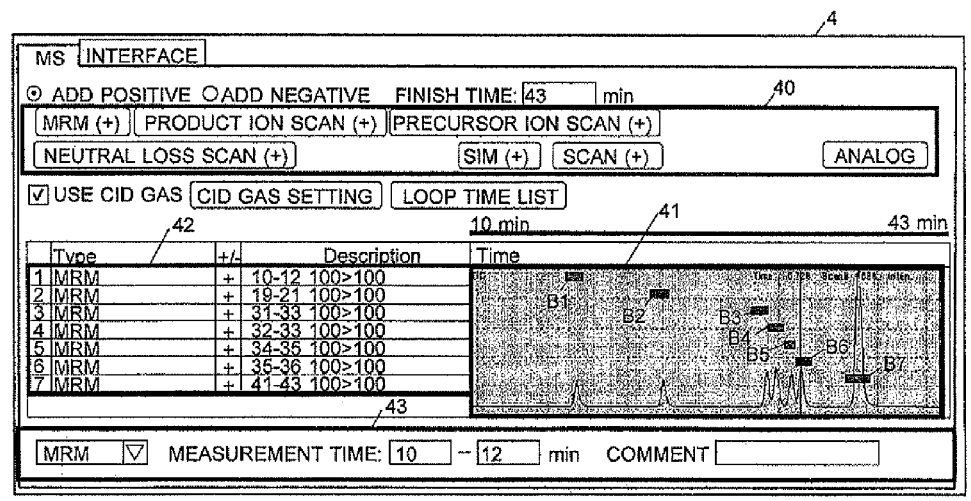
FIG. 4 shows an example of a loop time computational result window.

In the subsequent step (i.e. Step S7), the measurement time range setting section 31 provisionally sets the width of each of the peaks that have been detected in Step S6 as their measurement time range (FIG. 4). However, the operation of Step S7 moves to the next step (i.e. Step S8) in a very short time. Therefore, the user does not actually see the screen as shown in FIG. 4.

In comparison to the chromatogram display screen 4 in FIG. 3 (i.e. at the point in time when Step S4 is completed), the chromatogram display screen 4 in FIG. 4 additionally includes a measurement condition name display area 42 and a measurement condition setting area 43.

As the measurement time range setting section 31 sets the measurement time range for each peak in Step S7, range bars, each of which visualizes the time range of each measurement, are set so as to be superimposed on the reference chromatogram displayed in the chromatogram display area 41. In the example of FIG. 4, a total of seven measurements, all of which are an "MRM" measurement, have been set with measurement numbers 1 through 7 as shown in the measurement condition name display area 42. Range bars B1 through B7 which respectively correspond to the measurement numbers 1 through 7 are displayed in such a manner that they are superimposed temporally (i.e. in the horizontal direction) on the reference chromatogram displayed in the measurement time range display area 41. Each of the range bars B1 through B7 is visualized with a horizontal length that corresponds to the period of time for performing the measurement at a position corresponding to the aforementioned time range in the temporal axis direction (i.e. horizontal direction) of the reference chromatogram.

The range bars B1 through B7 which respectively correspond to the measurement numbers 1 through 7 are displayed with a shift in the intensity axis direction (i.e. vertical direction) in order for the range bars not to overlap each other.

In the subsequent step (i.e. Step S8), the measurement time range setting section 31 performs a specific operation on each peak. The process performed by the measurement time range setting section 31 in Steps S6 through S8 will now described in detail with reference to the schematic diagrams of FIGS. 5A-5C.

Figure 5A:
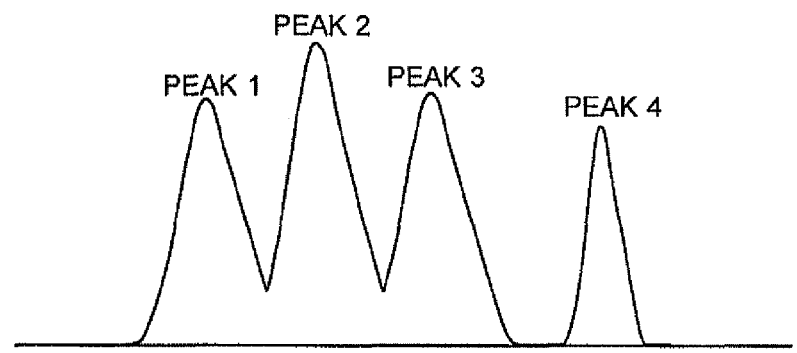
FIGS. 5A-5C are schematic diagrams showing the measurement time range setting section in operation.

Now suppose that a reference chromatogram includes Peak 1, Peak 2, Peak 3, and Peak 4, a total of four peaks, as shown in FIG. 5A. In Step S6, the measurement time range setting section 31 performs a waveform separation to detect the existence of these four peaks. When the measurement time range setting section 31 separates each peak, it also determines the width of the peak (the distance between the two edges of the peak).

Figure 5B:
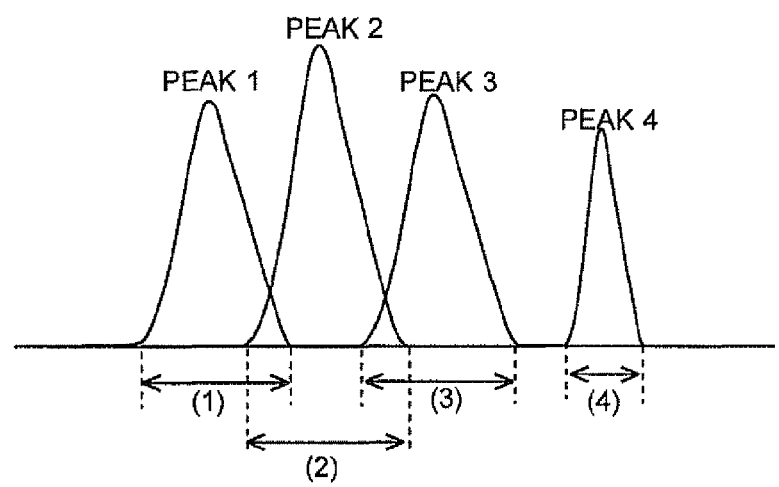

In Step S7, as shown in FIG. 5B, the measurement time range setting section 31 provisionally sets the width of each of the peaks which have been separated in Step S6 as its measurement time range. FIG. 5B shows that the measurement time ranges (1), (2), (3), and (4) have been provisionally set to Peak 1, Peak 2, Peak 3, and Peak 4, respectively.

Figure 5C:
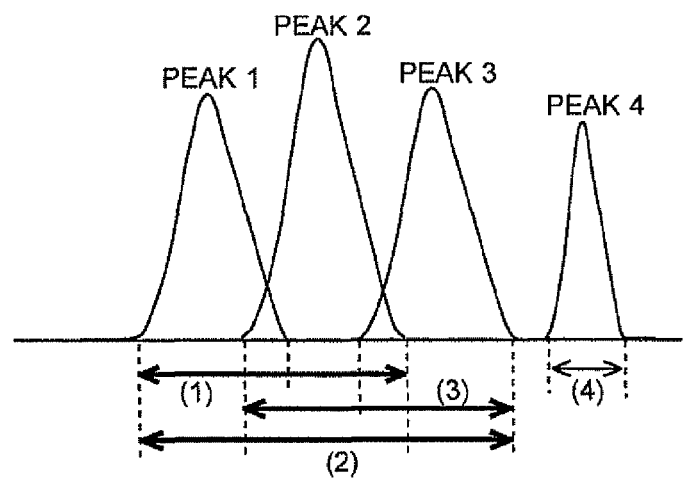

Subsequently, in Step S8, the measurement time range setting section 31 determines for each peak whether or not there is any overlapping peak that overlaps the peak. If an overlapping peak is detected, the overall width of the peak and the overlapping peak from end to end is newly set as the measurement time range of the peak. In FIG. 5B for example, Peak 2 overlaps Peak 1. Therefore, as shown in FIG. 5C, the length from the left end of Peak 1 to the right end of Peak 2 is set as the measurement time range (1) of Peak 1. Peak 1 and Peak 3 overlap Peak 2. Therefore, as shown in FIG. 5C, the length from the left end of Peak 1 to the right end of Peak 3 is set as the measurement time range (2) of Peak 2. Peak 2 overlaps Peak 3. Therefore, as shown in FIG. 5C, the length from the left end of Peak 2 to the right end of Peak 3 is set as the measurement time range (3) of Peak 3.

In Step S8, if no peak is found that overlaps a peak, the measurement time range setting section 31 sets the width of the peak which has been provisionally set in Step S7 as its measurement time range, without changing the measurement time range of the peak. In FIGS. 5A-5C, no peaks overlap Peak 4. Therefore, as shown in FIG. 5C, the width of Peak 4 itself is ultimately set as the measurement time range (4) of Peak 4.

Figure 6:
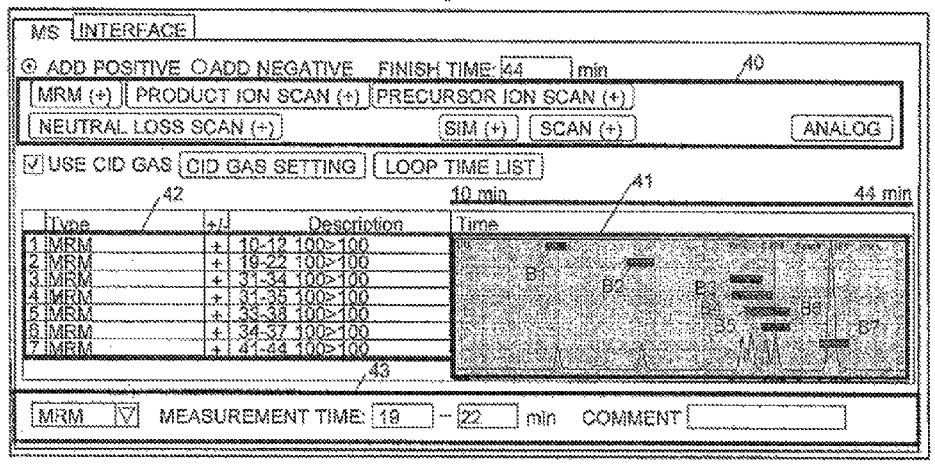
FIG. 6 is an example of a chromatogram display screen showing the result of an operation of the measurement time range setting section.
Figure 7:
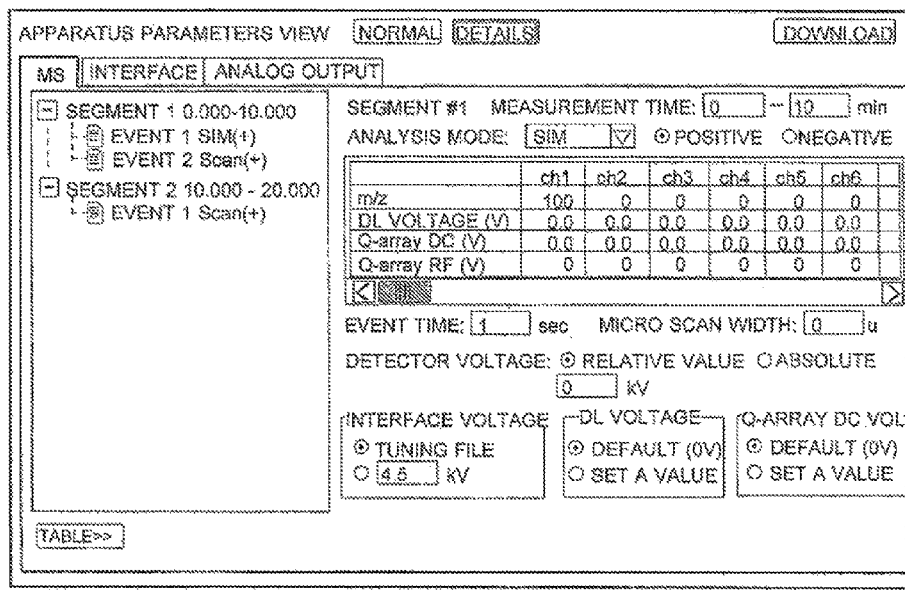
FIG. 7 shows an example of a screen of a conventional analyzing apparatus control application.

FIG. 6 shows an example of the chromatogram display screen 4 after the measurement time range of each peak has been newly set as previously described. It shows that an appropriate measurement time range has been set for each peak.

The analyzing apparatus control system according to the present invention has been described by using an embodiment. It should be noted that the embodiment described thus far is merely an example, and it is evident that any appropriate modification, adjustment, or addition can be made within the spirit of the present invention. Below are some example modifications.

In the aforementioned example, a measurement has been set for all peaks. However, a user may manually set a measurement time range for a peak to be measured, which may then be used as the provisionally set measurement time range by the measurement time range setting section 31 which performs the process of Step S8 as previously described.

In step S8, all peaks overlapping the peak for which a measurement time range is set may be considered as overlapping peaks by the measurement time range setting section 31. Alternatively, only two peaks may be taken into consideration, one before the peak and one after, as the overlapping peaks when newly setting the measurement time range.

After the measurement time ranges have been set for all peaks by the measurement time range setting section 31, the user may manually change (newly set) any of the measurement time ranges. In this case, the system of JP-A 2011-058982, which is an invention of the inventor of the present invention, can be preferably used.

EXPLANATION OF NUMERALS

1 . . . Analyzing Apparatus Control System
10 . . . CPU
12 . . . Memory
14 . . . Monitor
16 . . . Input Unit
18 . . . I/F
20 . . . Memory Unit
21 . . . Program for Analyzing Apparatus Control Unit
22 . . . Reference Chromatogram Memory Unit 23 . . . OS
31 . . . Measurement Time Range Setting Section
A1 . . . Analyzing Apparatus

The invention claimed is:

1. An analyzing apparatus and control system, comprising:

an analyzing apparatus including a chromatograph for temporally separating a sample to be examined, and performing a predetermined measurement in each of one or more measurement time ranges on an area where a peak exists in a chromatogram used for the predetermined measurement within a total measurement time; and a control system connected to the analyzing apparatus, wherein the control system includes a measurement time range setting section for detecting peaks included in a reference chromatogram which corresponds to the sample to be examined; for setting, for each of all detected peaks or previously selected peak or peaks included in the reference chromatogram, when a peak of the reference chromatogram does not overlap another peak of the reference chromatogram, a width of the peak of the reference chromatogram as a measurement time range of the peak of the chromatogram used for the predetermined analysis, or, when a peak of the reference chromatogram overlaps another peak of the reference chromatogram, an overall width of the peak of the reference chromatogram and at most two overlapped peaks of the reference chromatogram, one before and/or one after the peak of the reference chromatogram, as a measurement time range of the peak of the chromatogram used for the predetermined measurement by performing a waveform separation of the reference chromatogram; and for providing the measurement time range of the peak to set the one or more measurement time ranges of the predetermined measurement.

2. The analyzing apparatus and control system according to claim 1, wherein the analyzing apparatus is a chromatograph mass spectrometer.

3. The analyzing apparatus and control system according to claim 1, wherein the control system comprises a memory, a monitor, an input unit, a memory unit, an interface, and a CPU, the CPU is connected to the memory, the monitor, the input unit, the memory unit, and the interface which is connected to the analyzing apparatus.

* * * * *